(12) United States Patent
Vasanthan et al.

(10) Patent No.: US 7,566,470 B2
(45) Date of Patent: Jul. 28, 2009

(54) GRAIN FRACTIONATION METHODS AND PRODUCTS

(75) Inventors: Thavaratnam Vasanthan, Edmonton (CA); Feral Temelli, Edmonton (CA)

(73) Assignee: Governors of the University of Alberta, The (CA)

( * ) Notice: Subject to any disclaimer, the term of this patent is extended or adjusted under 35 U.S.C. 154(b) by 165 days.

(21) Appl. No.: 10/380,739

(22) PCT Filed: Sep. 26, 2001

(86) PCT No.: PCT/CA01/01358
§ 371 (c)(1),
(2), (4) Date: Jul. 21, 2003

(87) PCT Pub. No.: WO02/27011
PCT Pub. Date: Apr. 4, 2002

(65) Prior Publication Data
US 2004/0101935 A1 May 27, 2004

(30) Foreign Application Priority Data
Sep. 27, 2000 (CA) .................................. 2321315
Apr. 26, 2001 (CA) .................................. 2345606

(51) Int. Cl.
*A23L 1/10* (2006.01)

(52) U.S. Cl. .................. 426/436; 426/615; 426/429; 426/52; 435/101

(58) Field of Classification Search ............... 426/615, 426/429, 436, 52; 435/101
See application file for complete search history.

(56) References Cited

U.S. PATENT DOCUMENTS

| | | | |
|---|---|---|---|
| 3,912,590 A | 10/1975 | Slott et al. | |
| 3,950,543 A | 4/1976 | Buffa et al. | |
| 4,018,936 A | 4/1977 | Garbutt et al. | |
| 4,154,728 A | 5/1979 | Oughton | |
| 4,211,801 A | 7/1980 | Oughton | |
| 4,431,674 A | 2/1984 | Fulger et al. | |
| 4,804,545 A | 2/1989 | Goering et al. | |
| 5,013,561 A | 5/1991 | Goering et al. | |
| 5,063,078 A | 11/1991 | Foehse | |
| 5,082,673 A | 1/1992 | Inglett | |
| 5,106,634 A | 4/1992 | Thacker et al. | |
| 5,106,640 A | 4/1992 | Lehtomaki et al. | |
| 5,169,660 A | 12/1992 | Collins et al. | |
| 5,183,677 A | 2/1993 | Lehtomaki et al. | |
| 5,312,636 A | 5/1994 | Myllymaki et al. | |
| 5,312,739 A | 5/1994 | Shaw | |
| 5,458,893 A | 10/1995 | Smith | |
| 5,512,287 A | 4/1996 | Wang et al. | |
| 5,518,710 A | 5/1996 | Bhatty | |
| 5,580,762 A * | 12/1996 | Karube et al. | ............ 435/99 |
| 5,614,242 A | 3/1997 | Fox | |
| 5,725,901 A | 3/1998 | Fox | |
| 5,846,590 A * | 12/1998 | Malkki et al. | ............ 426/443 |
| 6,083,547 A | 7/2000 | Katta et al. | |
| 6,113,908 A | 9/2000 | Paton et al. | |
| 6,197,952 B1 | 3/2001 | Fox | |

FOREIGN PATENT DOCUMENTS

| | | | |
|---|---|---|---|
| EP | 377 530 | | 11/1990 |
| JP | 55118388 A | * | 9/1980 |
| JP | 02-222658 | | 9/1990 |
| JP | 03-206893 | | 9/1991 |
| JP | 03-285653 | | 12/1991 |
| JP | 07-501216 | | 2/1995 |

OTHER PUBLICATIONS

Izydorczyk, MS et al. Variation in total and solube beta-glucan content in hulless barley: effects of thermal, physical and enzymic treatment. J. Agric. Food Chem. 2002. 48: 982-989.*
Tunga, R et al. Some studies on optimization of extraction process for protease production in SSF. Bioprocess Engineering. 1999. 20: 485-489.*
Simon, LM et al. Stability of hydrolytic enzymes in water-organic solvent systems. Journal of Molecular Catalysis B: Enzymatic. 1998. 4: 41-45.*
Chitradon, L et al. Oligosaccharide synthesis by reversed catalysis using alpha-amylase from *Bacillus licheniformis*. Journal of Molecular Catalysis B: Enzymatic. 2000. 10:273-280.*
Simon, LM et al. The effects of organic solvent/water mixtures on the structure and catalytic activity of porcine pepsin. Process Biochemistry. 2007. 42: 909-912.*
"Activity and action pattern of *Bacillus licheniformis* α-amylase in aqueous ethanol", Anthony B. Blakeney and Bruce A. Stone, Jul. 1985.
"Studies on oat gum [(1→3, 1→4)-β=D-glucan]: composition, molecular weight estimation and rheological properties", N.L. Dawkins and I.A. Nnanna, 1995.
"Extraction and Enrichment of (1→3), (1→4)-β-D-Glucan from Barley and Oat Brans", R.S. Bhatty, 1993.
"Large-Scale Preparation and Properties of Oat Fractions Enriched in (1→3)(1→4)-β-D-Glucan", Peter J. Wood, John Weisz, Paul Fedec and Vernon D. Burrows, 1989.

* cited by examiner

*Primary Examiner*—Leon B. Lankford, Jr.
*Assistant Examiner*—Susan E. Fernandez
(74) *Attorney, Agent, or Firm*—Squire, Sanders & Dempsey L.L.P.

(57) ABSTRACT

The invention generally relates to a method for fractionating plant material into valuable components including beta-glucan. The method uses an organic solvent and water instead of water alone, acidified water and/or aqueous alkali as a solvent for the slurrying of a grain flour. In addition to concentrating beta-glucan, other product fractions produced by the method include starch concentrate, and organic solvent solubles. If enzyme treatments are used, other product fractions include dextrin, protein hydrolysates and organic solvent solubles. The process is particularly effective in concentrating beta-glucans in a state close to its native form from the endosperm of barley and oat grains.

18 Claims, 3 Drawing Sheets

Fig 1

Fig 2: Front End Dry Processing of Barley/Oat Grains

Fig 3: Fractionation of Barley/Oat in Aqueous Ethanol

GRAIN FRACTIONATION METHODS AND PRODUCTS

FIELD OF THE INVENTION

This invention relates to methods for secondary processing of plant material and in particular for the recovery of valuable products such as fiber including beta-glucan, starch, protein and ethanol solubles from plant material containing starch and fiber.

BACKGROUND OF THE INVENTION

Plant materials including grains contain a number of valuable components such as starch, protein, mixed linkage 1-4, 1-3 beta-D-glucan (beta-glucan), cellulose, pentosans, tocols, etc. These components, and products derived from these components, have many food and non-food uses. Consequently, there is a strong and continued industry interest for the processing of such plant materials.

Using barley grain as an example, the beta-glucan (usually up to 8% w/w) therein exists as a major component of the endosperm cell walls, with other minor components such as cellulose and hemi-cellulose (pentosans). The beta-glucan has many potential applications in the food (i.e. functional foods), pharmaceutical and cosmetic industries. Nutritional studies have suggested that inclusion of beta-glucan and tocols (i.e. tocopherol and tocotrienol) into the human diet will benefit human health.

The starch (up to 65%) in barley shows comparable functionality (i.e. thickening, gelling, paper making qualities, acid/enzyme resistance, etc.) to corn starch, which is currently used extensively for various applications. Therefore, barley starch can be substituted for corn starch in the preparation of many existing food and industrial products (i.e. modified food starches, cationic or amphoteric starches for paper industry, dextrin's for food and paper industry, adhesives, acid cut starches, etc.). Because of the aforementioned reasons, a strong and continued industry interest currently exists for the fractionation and utilization of barley grain.

A number of investigations at laboratory and pilot scale have been carried out on the fractionation of barley. In general, water, acidified water and/or aqueous alkali (i.e. NaOH or $NaHCO_3$) have been used as a solvent for the slurrying of whole cracked barley, barley meal (milled whole barley) or barley flour (roller milled barley flour or pearled-barley flour). The slurry is then processed by techniques such as filtration, centrifugation and ethanol precipitation to separate the slurry into various components. This conventional process for barley fractionation has a number of technical problems and whilst realizing limited commercial feasibility has been limited by the expense of the product particularly for food applications.

In particular, technical problems arise because the beta-glucan in barley flour is an excellent water-binding agent (a hydrocolloid) and as such, upon addition of water (neutral, alkali or acidic environment), the beta-glucan hydrates and tremendously thickens (increases the viscosity) the slurry. This thickening imposes many technical problems in the further processing of the slurry into pure barley components (i.e. starch, protein, fiber, etc.), including clogging of the filter during filtration and inefficient separation of flour components during centrifugation.

Usually, these technical problems are minimized, if not eliminated, by the addition of a substantial quantity of water to the thick/viscous slurry in order to dilute and bring the viscosity down to a level where further processing can be carried out. However, the use of high volumes of water leads to several further problems including increased effluent water volumes and the resulting increased disposal costs. In addition, the beta-glucan, which solubilizes and separates with the supernatant (water) during centrifugation, is usually recovered by precipitation with ethanol. This is done by the addition of an equal volume of absolute ethanol into the supernatant. After the separation of precipitated beta-glucan, the ethanol is preferably recovered for recycling. However, recovery requires distillation, which is also a costly operation from an energy usage perspective.

Accordingly, there has been a need for an efficient process for the fractionation of grains which overcomes the particular problems of slurry viscosity and water usage. Moreover, there has been a need for a process which provides a high purity beta-glucan product with decreased starch and protein content.

More specifically, there has been a need for a grain fractionation process wherein a grain or grain flour is slurried in a solvent wherein beta-glucan is recovered without solubilization and wherein the solvent used for slurrying the grain or grain flour may be efficiently recycled.

A review of the prior art reveals that such a process has not been heretobefore realized. For example, there are numerous previous patents which describe various methods of fractionating grain through the above mentioned solubilization and subsequent ethanol precipitation methodology. Examples of such patents include U.S. Pat. No. 4,018,936 (Garbutt et al.), U.S. Pat. No. 5,512,287 (Wang et al.) U.S. Pat. No. 5,614,242, U.S. Pat. No. 5,725,901 (Fox), U.S. Pat. No. 6,197,952 (Fox), U.S. Pat. No. 6,113,908 (Paton et al), U.S. Pat. No. 5,169,660 (Collins), U.S. Pat. No. 5,312,636 (Myllymiaki), U.S. Pat. No. 5,518,710 (Bhatty), and U.S. Pat. No. 5,846,590 (Malkki).

Other patents also teach the use of amylase enzymes for hydrolysing starch during grain processing including U.S. Pat. No. 4,804,545 (Goering), U.S. Pat. No. 5,013,561 (Goering et al.), U.S. Pat. No. 5,082,673 (Inglett) and U.S. Pat. No. 3,912,590 (Slott).

Other patents are directed to mechanically concentrating beta-glucans by size reduction and sieving/air classification practices and include U.S. Pat. No. 5,063,078 (Foehse), U.S. Pat. No. 5,725,901 (Fox), and U.S. Pat. No. 6,083,547 (Katta).

Other patents are directed to the use of low concentration ethanol solutions in recovering beta-glucan and include U.S. Pat. Nos. 5,106,640 and 5,183,677 (Lehtomaki).

Still other patents are directed to miscellaneous grain fractionation techniques such as U.S. Pat. No. 5,106,634 (Thacker) U.S. Pat. Nos. 4,211,801 and 4,154,728 (Oughton) U.S. Pat. No. 3,950,543 (Buffa) U.S. Pat. No. 4,431,674 (Fulger) U.S. Pat. No. 5,312,739 (Shaw).

SUMMARY OF THE INVENTION

The invention generally relates to a method for fractionating plant material such as barley and oat into valuable components including beta-glucan. The method uses an organic solvent and water instead of water alone, acidified water and/or aqueous alkali as a solvent for the slurrying of a grain flour.

In accordance with the invention, there is provided a method of obtaining fiber or beta-glucan from plant materials comprising the steps of a) mixing and incubating a plant material flour with an aqueous organic solvent in a single step; and, b) separating the mixture from step a) to form a filtrate portion and a retentate portion; wherein the retentate portion has a high fiber or beta-glucan content.

In accordance with a further embodiment step a) further includes incubating the mixture with any one of or a combination of amylase or protease enzymes.

In further embodiments of the invention the plant material flour is selected from any one or a combination of barley and oat and/or the organic solvent is selected from methanol, ethanol, propanol or butanol or a mixture thereof.

In a more specific embodiment the solvent is ethanol and the ethanol solution concentration in step a) is 10-100% (v/v) and preferably 40-50% (v/v).

The method is conducted at a temperature of 15-60° C. and preferably at room temperature.

The particle size of the plant material flour is preferably controlled for obtaining a higher yield and concentration as desired wherein >80% of the flour is <250 microns, >85% of the flour is <250 microns, >90% of the flour is <250 microns or >95% of the flour is <250 microns.

In another embodiment the slurry is separated by a screen having a screen size between 40-250 microns and preferably between 40-75 microns.

In a still farther embodiment, the flour to aqueous organic solvent ratio is 1:2 to 1:10 (w/v).

With respect to farther embodiments of the method, step a) may be repeated recycling the aqueous organic solvent of the filtrate portion from step b).

Further still, the retentate portion of step b) may be subjected to at least one subsequent wash with aqueous organic solvent and separation to form subsequent filtrate and retentate portions. Subsequent washing steps may also include incubating the mixture with any one of or a combination of amylase or protease enzymes.

In accordance with the invention, a beta-glucan concentrate from barley having a beta-glucan concentration of 40-70% by weight is provided which may have a starch concentration of 1-40%.

In a further embodiment of the method, the filtrate portion is further evaporated to form a distillate portion containing organic solvent and a product solids portion containing starch and organic solvent solubles. In the case where the method includes enzyme treatment the filtrate portion may be further evaporated to form a distillate containing organic solvent and a product solids portion containing dextrin, protein hydrolysates and organic solvent solubles.

Further still, the invention provides a beta-glucan concentrate from barley, oat or a mixture thereof prepared by a process which comprises the steps of: a) mixing and incubating a barley or oat flour or a mixture thereof with an aqueous organic solvent in a single step; and, b) separating the mixture from step a) to form a filtrate portion and a retentate portion; wherein the retentate portion has a high beta-glucan content.

BRIEF DESCRIPTION OF THE DRAWINGS

The invention is described with reference to the following drawings in which.

DETAILED DESCRIPTION OF THE INVENTION

Overview

Figure 1:
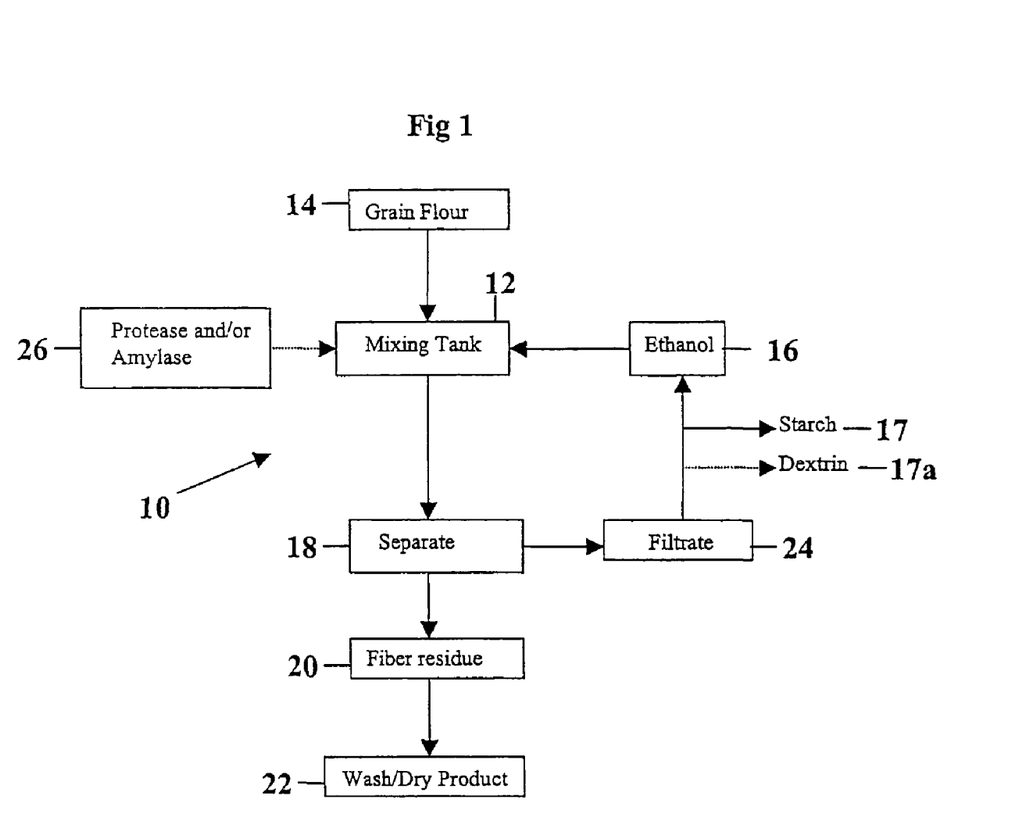
FIG. 1 is a flow diagram showing one method for processing a plant material flour in accordance with the invention.
Figure 2:
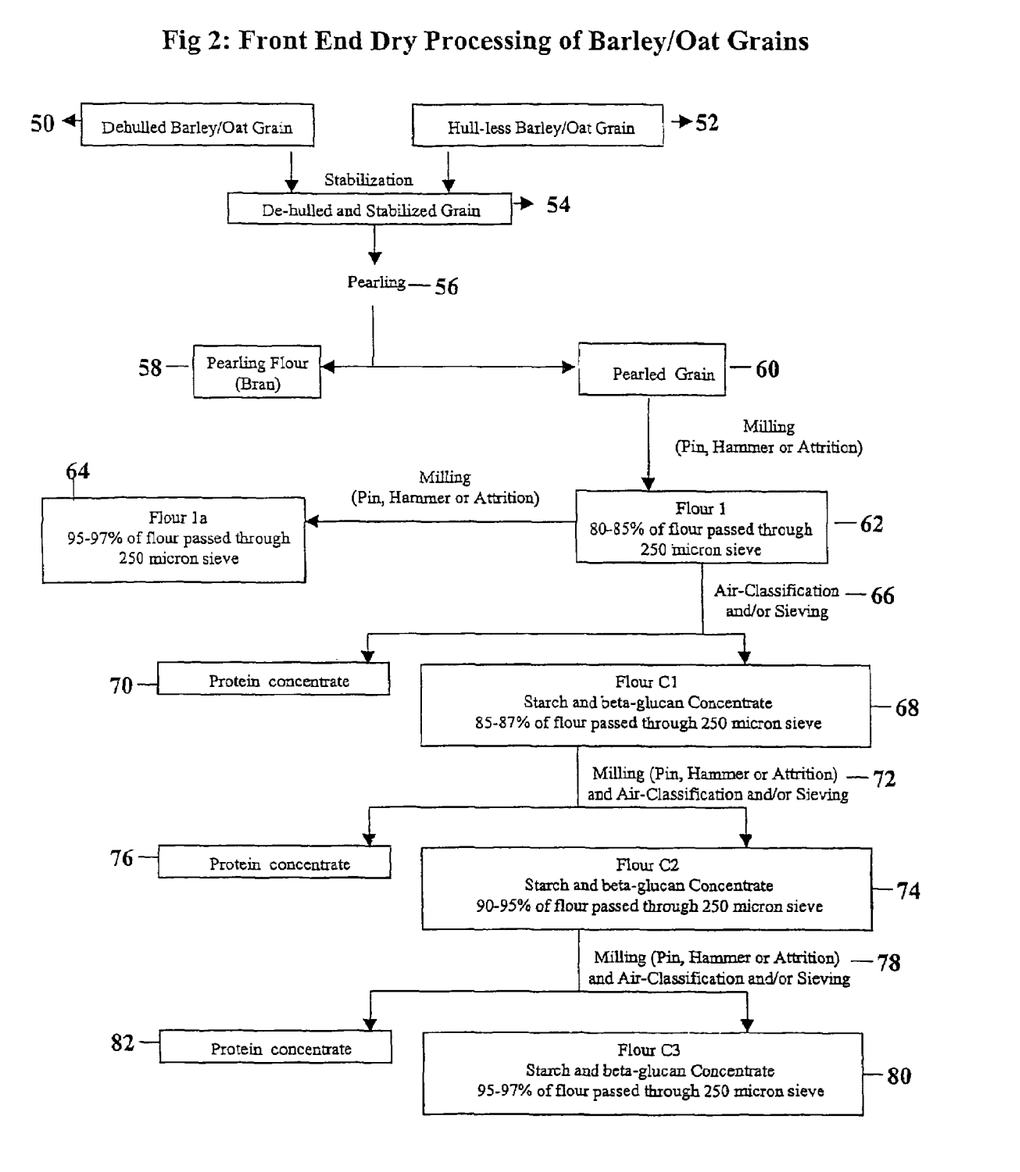
FIG. 2 is a flow diagram of a front-end process for preparing plant material flours for use in accordance with the invention; and, FIG. 3 is a flow diagram showing a further method for processing a plant material flour in accordance with the invention.
Figure 3:
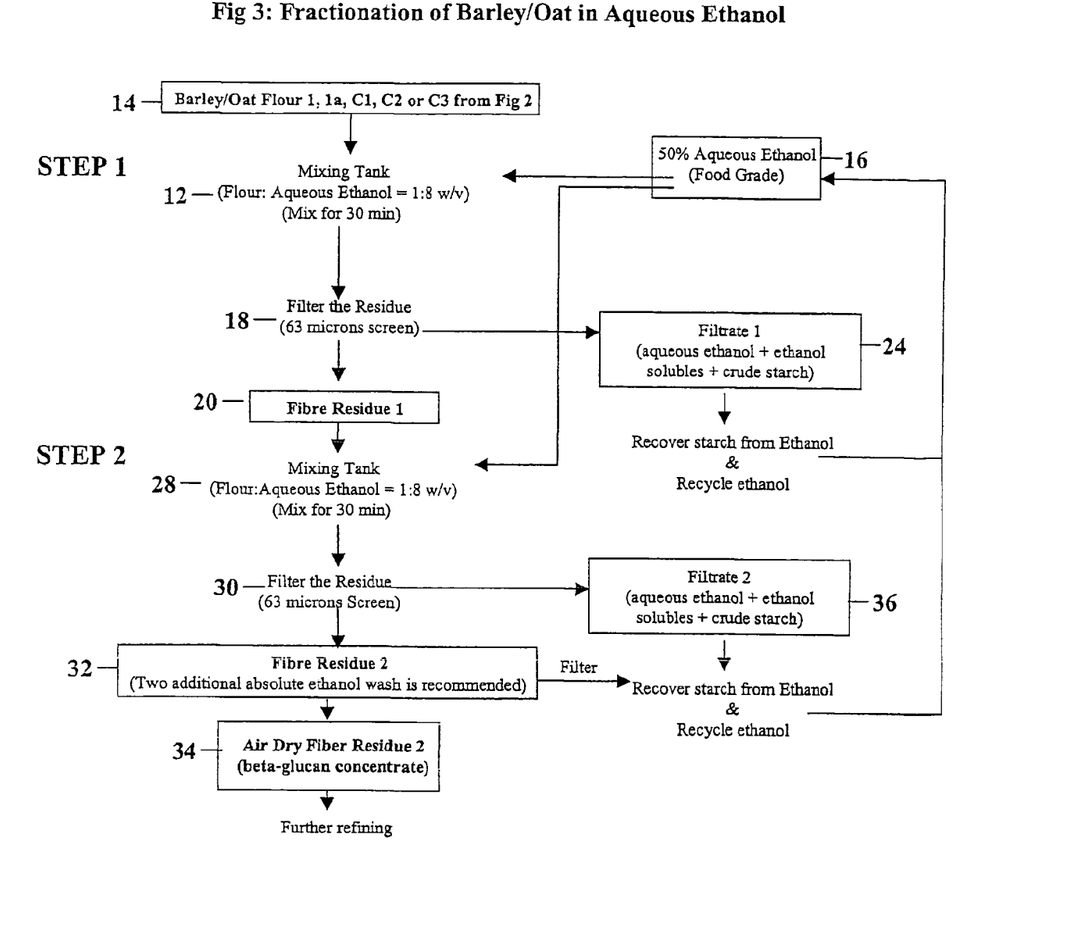

With reference to FIGS. 1-3, a process 10 for concentrating beta-glucan without solubilization of the beta-glucan molecule is described. The process involves direct slurrying and mixing in a tank 12 of a plant material flour (preferably a grain flour) 14 in an organic solvent 16 (preferably aqueous ethanol) and separating 18 a solid fiber concentrate 20 containing beta-glucan from the slurry. The fiber concentrate 20 containing beta-glucan is washed, dried and milled 22 to produce a high concentration beta-glucan product. The filtrate 24 containing starch and organic solvent solubles may be recycled to the mixing tank 12 after separation of starch. The process may optionally include a treatment with protease and/or amylase enzymes 26 for further improving the concentration of beta-glucans in the fiber/beta-glucan concentrate by additional protein and/or starch removal to provide a beta-glucan concentrate having less protein or starch.

In accordance with the invention, a fiber product enriched in beta-glucan, which is light in color and bland in flavor, for food and non-food (including cosmetic, medical, pharmaceutical) applications can be produced.

In addition to concentrating beta-glucan, other product fractions produced by the method include starch concentrate 17, and organic solvent solubles. If enzyme treatments are used, other product fractions include dextrin, protein hydrolysates and organic solvent solubles.

The process is particularly effective in concentrating beta-glucans in a state close to its native form from the endosperm of barley and oat grains.

Dry Processing of Raw-Materials

The raw-materials for use in the process include cereal grain meal, flour or bran produced by a variety of traditional dry processing techniques as outlined in FIG. 2. As used herein, "meal" means the ground/milled whole grain (hulled, dehulled or hull-less grain), "flour" means the grain powder that is produced from the whole grain using techniques such as milling, sieving, air-classification, sifting, eat., but does not contain 100% of the whole grain components and "bran" means the outer grain tissue layers, except the hulls, especially down to sub-aleurone and endosperm layers immediately below the sub-aleurone layer.

As shown in FIG. 2, different flour fractions can be created using different dry processing techniques. Dehulled 50 or hull-less 52 barley or oat grains are optionally heat treated to produce stabilized grain 54. The heat stabilization is conducted in order to inactivate the endogenous enzymes such as lipase, lipoxygenase, amylase, beta-glucanase, protease, etc. which may contaminate different fractions and lead to molecular degradation of various product fractions.

Pearling 56 produces a pearling flour (bran) 58 and a pearled grain 60. Pearling is preferably conducted in a SATAKE or disk-type pearler to specific levels depending on the grain. For example, the optimum level of pearling for oat and barley may be approximately 12% and 32%, respectively depending on the specific variety. If pearled much beyond these limits, there is significant beta-glucan loss. However, barley and oat can be pearled to any extent and both pearling-flour and pearled-grain (as it is or after grinding/milling) can be used for further fractionation processing.

The pearled grain 60 is milled to produce a flour 62 (designated flour 1) having a particle size where >80-85% of the flour pass through a 250 micron sieve. A finer fraction 64

(designated flour 1a) may be produced by further milling wherein >90-95% of the flour pass through the 250 micron sieve.

Air classification/sieving 66 of the flour 1 fraction produces a flour 68 (designated flour C1) where >85-87% of the flour pass through the 250 micron sieve and a larger particle size fraction 70 having a higher protein concentration.

Further milling and air classification/sieving 72 of the flour C1 produces a flour 74 (designated C2) having a particle size where >90-95% of the flour pass through the 250 micron sieve and a larger particle size fraction 76 having a higher protein concentration.

Still further milling and air classification/sieving 78 of the flour C2 produces a flour 80 (designated C3) having a particle size where >95-97% of the flour pass through the 250 micron sieve and a larger particle size fraction 82 having a higher protein concentration.

Milling may be pin, hammer or attrition milling as is understood by those skilled in the art.

The various flours formed by successive milling and air classification techniques will affect the yield and purity of the beta-glucan product. That is, to achieve the optimum yield and beta-glucan concentration of the fiber concentrate, by aqueous ethanol slurrying and screening process, control of the particle size is important. For example, it was determined that the flour containing a higher proportion of fine particles (<50 microns in diameter), prepared by repeated milling will reduce the yield of fiber concentrate. In contrast, the flour containing a higher proportion of coarser particles (>250 microns in diameter), prepared by a single milling, will reduce the beta-glucan concentration of the fiber concentrate. Any combination of milling, sieving, and air classification steps can be used as is understood by those skilled in the art to achieve the appropriate particle size distribution needed for further processing.

Preferably, the flour also contains little or no bran as the phenolic compounds and enzymes within bran may cause discoloration of the final product.

Experimental

As illustrated in FIGS. 1 and 3 and described generally above, experimental detail of the slurrying, screening, enzyme treatments, recycling, post-treatments and examples are provided.

Slurrying

The grain fraction (i.e. meal, flour, bran, etc), as prepared through any combination of dry techniques discussed above, was slurried in aqueous ethanol (10-100% (v/v) but preferably between 40-50% (v/v)) at range of temperatures (15-50 degree C., and preferably room temperature to realize efficient energy consumption) for varying periods of time but preferably 10-30 min. The fiber/beta-glucan concentrate was recovered from the slurry by screening/filtering described below. Also, the grain (i.e. whole, pearled, cracked, coarsely ground, etc) can be directly mixed with aqueous ethanol and comminuted (wet-milled) to finer particles and slurried using an in-line macerator.

Other organic solvents including methanol, propanol or butanol or a mixture thereof may be utilized.

Screening

The slurry was screened using a TYLER screen/sieve. The retentate (fiber/beta-glucan concentrate) was collected from the sieve, washed in excess ethanol and dried. The screen size should be selected according to the raw material (i.e. meal, flour, bran, comminuted/macerated grain, etc) particle size and can range from 40-250 microns as a relationship was observed between the flour particle size, screen size, beta-glucan yield and concentration. For example, the use of a TYLER 250 (63 microns) screen was found to be particularly effective in optimizing beta-glucan yield. A filter size below 40 microns increased separation times by slowing down ethanol flow through the screen. The use of screen size above 75 microns decreased the yield of beta-glucan concentrate and increased the fiber content within the filtrate.

The use of multiple screens will improve the recovery of fiber/beta-glucan concentrate and will also lead to multiple fiber products based on their particle size.

Other methods such as centrifugation may be used in place of filtration to separate the fiber residue from the filtrate, however, more complex equipment or methods may be required to further separate other compounds from the fiber.

The effect of grain fraction particle size on the recovery and composition of the fiber/beta-glucan concentrate obtained by screening is presented in Table 1.

TABLE 1

The influence of flour[1] particle size on the beta-glucan content of fiber concentrate that is obtained by aqueous ethanol-wash[2]

| | Flour | | Air Dried Fiber Residue[5] | |
|---|---|---|---|---|
| Sample | % Beta-glucan (w/w, db) | Particle size description [% (w/w) of flour with particle size <250 microns] | % Yield[6] (w/w, db) | % Beta-glucan[7] (w/w, db) |
| OAT (DEHULLED) | | | | |
| Whole grain/groats | 3.5[3] | | | |
| Flour 1 | 3.6 | 80-85 | 12-13 | 24-25 |
| Flour 1a | 3.6 | 95-97 | 10-11 | 31-32 |
| Flour C1 | 5.1 | 85-87 | 14-15 | 26-27 |
| Flour C2 | 6.0 | 90-95 | 14-15 | 28-29 |
| Flour C3 | 7.3 | 95-97 | 20-21 | 31-32 |
| Whole grain/groats | 7.9[4] | | | |
| Flour 1 | 7.9 | 80-85 | 25-26 | 29-30 |
| Flour 1a | 7.9 | 95-97 | 22-23 | 32-33 |
| HULL-LESS BARLEY | | | | |
| Whole grain/groats | 7.0[4] | | | |
| Flour 1 | 7.8 | 80-85 | 30-31 | 23-24 |
| Flour 1a | 7.8 | 95-97 | 19-20 | 33-34 |
| Flour C1 | 9.4 | 85-87 | 31-32 | 28-29 |
| Flour C2 | 11.5 | 90-95 | 28-29 | 34-35 |
| Flour C3 | 13.4 | 95-97 | 35-36 | 35-36 |

[1]Flour was produced by the protocol outlined in FIG. 2.
[2]Aqueous ethanol wash was carried out by the protocol outlined in FIG. 3.
[3]Regular variety
[4]High beta-glucan variety
[5]FIG. 3 - Box 34
[6]% Yield is the amount of fiber residue as a percentage of the starting amount of flour
[7]% Beta Glucan is the concentration of beta glucan within the air-dried fiber residue Recovery of beta-glucan in the air-dried fiber residue indicated that the size of most of the fiber particles in the raw material flour would be above 63 microns as explained in greater detail below.

Enzyme Treatment

Scanning electron microscopic examination of grain (i.e. barley and oat) meal/flour indicated that the fiber (including beta-glucan, cellulose, pentosans/hemi-cellulose) exists in close association with the protein matrix and starch granules and that most of the starch granules were embedded in the protein matrix.

As shown in FIG. 1, optional treatment with a protease and/or amylase enzyme 26 during ethanol slurrying 12 hydrolyzes the protein and starch that is in association with fiber and thereby liberates a higher amount of the fiber/beta-glucan and starch.

The preferred levels of enzyme is between 0.1-1%, w/w, protein or starch weight basis. The ratio between the raw material and aqueous ethanol can range from 1:2 to 1:20, preferably 1:8 (w/v). Reaction time may vary (typically 0.5 h to 1 day) based on and optimized for enzyme concentration, temperature (1-90° C.) and pH (typically 5.0-7.0, but not limited to this range).

Different protease (including papain, bromelain etc.) and amylase (including fungal amylase, termamyl, etc.) enzymes have been investigated at different temperatures ranging from 15-85° C. The results indicated that the enzymes varied in their proteolytic and amylolytic performance. Therefore, the choice of enzyme will depend on the cost and performance.

Recycling

The filtrate 24 from the screening separation contains aqueous ethanol along with other components including starch, dextrin (if amylase is used), protein, protein hydrolysates (if protease is used) some fiber, and alcohol solubles, etc. As shown in FIGS. 1 and 3, the ethanol is preferably recycled to the mixing tank 12. Starch or dextrin may be recovered from the filtrate by centrifugation prior to recycling or after a specific number of cycles.

Similarly, the ethanol may be periodically distilled to recover other alcohol solubles. Recovered dextrin or alcohol solubles may be further purified or processed.

Post-treatment

The residue 20 from separation contains fiber and, in particular, is concentrated in beta-glucan. The residue 20 can be dried to produce a powder for further applications: When it is desired that a higher purity beta-glucan product is required, further purification of the residue may be conducted.

With reference to FIG. 3, the fiber residue 20 can be processed to remove additional starch by repeating the ethanol wash process. As shown in FIG. 3, at step 2, the residue is mixed 28 with aqueous ethanol to create a slurry and re-filtered 30 to create a fiber residue 32 and filtrate 36. Step 2 may be repeated as necessary. Step 2 may also include an enzyme treatment as described above.

Fiber residues 20, 34 can be additionally treated for incorporation into further products. If the residue is permitted to air dry, it tends to create a hard granular product because of the inclusion of water therein. Intensive milling is required in order to form a powder from the granulated product. Dehydration can be effected by slow oven drying after washing with a dehydrant organic solvent that will remove water contained therein without affecting the beta-glucan quality.

Other products 17a, such as crude dextrin may be dried, for example by spray drying, to create a crude dextrin powder that can be used for various applications such as food or feed formulations or non-food applications such as a binder/adhesive for example in the paper board industry. Starch 17 may be recovered by centrifugation. Ethanol solubles may be recovered by distillation.

EXAMPLES

Effect of Enzyme Treatments on the Yield (%) and Beta-glucan Concentration (%) of Fiber/Beta-glucan Concentrate Example 1

Aqueous Ethanol Slurrying at 20° C. for 30 min and Screening

Flour (100 g) was slurried in 800 ml of aqueous ethanol (50%, v/v), stirred at 20° C. for 30 min and screened (63 micron sieve) to recover the fiber/beta-glucan concentrate on the screen. The fiber concentrate was re-slurried and re-screened. The fiber/beta-glucan concentrate was subsequently washed with absolute ethanol and dried.

Example 2

Aqueous Ethanol Slurrying of Fiber/Beta-glucan Concentrate From Example-1 at 20° C. for 20 h and Screening The fiber/beta-glucan concentrate that was obtained in example-1 was slurried in aqueous ethanol (50%, v/v) (the ratio between fiber/beta-glucan concentrate and aqueous ethanol was 1:8 w/v), stirred at 20° C. for 20 h and screened (63 micron sieve) to recover the fiber/beta-glucan concentrate on the screen. The concentrate was re-slurried and re-screened. The fiber/beta-glucan concentrate was subsequently washed with absolute ethanol and dried.

Example 3

Same as Example-2, but with Stirring at 35° C.

The fiber/beta-glucan concentrate that was obtained in example-1 was slurried in aqueous ethanol (50%, v/v) (the ratio between fiber/beta-glucan concentrate and aqueous ethanol was 1:8 w/v), stirred at 35° C. for 20 h and screened (63 micron sieve) to recover the fiber/beta-glucan concentrate on the screen. The concentrate was re-slurried and re-screened. The fiber/beta-glucan concentrate was subsequently washed with absolute ethanol and dried.

Example 4

Protease Treatment Applied to Fiber/Beta-glucan Concentrate from Example-1 at 20° C.

The fiber/beta-glucan concentrate that was obtained in example-1 was re-slurried in aqueous ethanol (50%, v/v) (the ratio between fiber/beta-glucan concentrate and aqueous ethanol was 1:8 w/v) containing protease enzyme (1%, protein dry weight basis) and treated at 20° C. for 20 h. The slurry was then screened (63 microns sieve) to recover the fiber/beta-glucan concentrate, which was subsequently washed with absolute ethanol and dried.

Example 5

Protease Treatment Applied Directly to Flour at 20° C.

Flour (100 g) was slurried in 800 ml of aqueous ethanol (50%, v/v) and treated at 20° C. with protease enzyme (1%, protein dry weight basis) for 20 h. The slurry was then screened (63 microns) to recover fiber/beta-glucan concentrate, which was then reslurried, stirred at 20° C. for 30 minutes, re-screened and subsequently washed with absolute ethanol and dried.

Example 6

Same as Example-4, but with Protease Treatment at 35° C.

The fiber/beta-glucan concentrate that was obtained in example-1 was slurried in aqueous ethanol (50%, v/v) (the ratio between fiber/beta-glucan concentrate and aqueous ethanol was 1:8 w/v), containing protease enzyme (1%, protein dry weight basis) and treated at 35° C. for 20 h. The slurry was then screened (63 microns) to recover fiber/beta-glucan concentrate, which was then re-slurried, stirred at 20° C. for 30 minutes, re-screened and subsequently washed with absolute ethanol and dried.

Example 7

Alpha-amylase Treatment Applied to Fiber/beta-glucan Concentrate Obtained from Example-1

The fiber/beta-glucan concentrate that was obtained in example-1 was re-slurried in aqueous ethanol (50%, v/v) (the ratio between fiber/beta-glucan concentrate and aqueous ethanol was 1:8 w/v) containing alpha-amylase enzyme (1%, starch dry weight basis) and treated at 20° C. for 20 h. The slurry was then screened (63 microns) to recover fiber/beta-glucan concentrate, which was subsequently washed with absolute ethanol and dried.

Example 8

Protease and Alpha-amylase Treatments Sequentially Applied to Flour

The fiber/beta-glucan concentrate that was obtained in example-1 was re-slurried in aqueous ethanol (50%, v/v) (the ratio between fiber/beta-glucan concentrate and aqueous ethanol was 1:8 w/v) containing protease enzyme (1%, protein dry weight basis) and treated at 20° C. for 20 h. The slurry was then screened (63 microns) to recover fiber/beta-glucan concentrate, which was re-slurried in aqueous ethanol (50%, v/v) (the ratio between fiber/beta-glucan concentrate: ethanol was 1:8 w/v) containing alpha-amylase enzyme (1%, starch dry weight basis) and treated at 20° C. for 20 h. The slurry was then screened (63 microns) to recover fiber/beta-glucan concentrate, which was subsequently washed with absolute ethanol and dried.

Example 9

Same as Example 7 or 4 but with an Enzyme Mixture (Protease+Alpha-amylase)

The fiber/beta-glucan concentrate that was obtained in example-1 was re-slurried in aqueous ethanol (50%, v/v) (the ratio between fiber/beta-glucan concentrate and aqueous ethanol was 1:8 w/v) containing a mixture of protease enzyme (1%, protein dry weight basis) and alpha-amylase enzyme (1%, starch dry weight basis) and treated at 20° C. for 20 h. The slurry was then screened (63 microns) to recover fiber/beta-glucan concentrate, which was subsequently washed with absolute ethanol and dried.

Example 10

Same as Example 8, but with Thermostable Alpha-amylase

The fiber/beta-glucan concentrate that was obtained in example-1 was re-slurried in aqueous ethanol (50%, v/v) (the ratio between fiber/beta-glucan concentrate and aqueous ethanol was 1:8 w/v) containing protease enzyme (1%, protein dry weight basis) and treated at 20° C. for 20 h. The slurry was then screened (63 microns) to recover fiber/beta-glucan concentrate, which was re-slurried in aqueous ethanol (50%, v/v) (the ratio between fiber/beta-glucan concentrate: ethanol was 1:8 w/v) containing thermostable alpha-amylase enzyme (1%, starch dry weight basis) and treated at 80-85° C. for 1 h. The slurry was then screened (63 microns) to recover fiber/beta-glucan concentrate, which was subsequently washed with absolute ethanol and dried.

Example 11

Same as Example 7, but with Thermostable Alpha-amylase

The fiber/beta-glucan concentrate that was obtained in example-1 was re-slurried in aqueous ethanol (50%, v/v) (the ratio between fiber/beta-glucan concentrate and aqueous ethanol was 1:8 w/v) containing thermostable alpha-amylase enzyme (1%, starch dry weight basis) and treated at 80-85° C. for 1 h. The slurry was then screened (63 microns) to recover fiber/beta-glucan concentrate, which was subsequently washed with absolute ethanol and dried.

TABLE 2

Effect of enzyme treatments

| | Raw material | | Fiber/β-Glucan concentrate | | | | |
|---|---|---|---|---|---|---|---|
| Sample | β-glucan$^c$ % | TREATMENT | Yield % | β-Glucan$^c$ % | β-Glucan, Recovery$^d$ % | Protein$^e$ % | Starch$^f$ % |
| BARLEY | | | | | | | |
| Flour-1$^a$ | 7.84 | Example 1 | 30.3 | 23.6 | 88.4 | 8.0 | 51.8 |
| | | Example 2 | 27.9 | 25.6 | 87.4 | 8.1 | 53.2 |
| | | Example 4 | 13.0 | 54.9 | 91.6 | 7.4 | 19.8 |
| | | Example 5 | 12.6 | 55.9 | 85.3 | 6.8 | 19.8 |
| | | Example 10 | 13.3 | 51.7 | 84.4 | 5.8 | 26.0 |
| | | Example 11 | 19.8 | 34.6 | 85.9 | 9.8 | 34.7 |

TABLE 2-continued

Effect of enzyme treatments

| | Raw material | | Fiber/β-Glucan concentrate | | | | |
|---|---|---|---|---|---|---|---|
| | | | | β-Glucan, | | | |
| Sample | β-glucan[c] % | TREATMENT | Yield % | β-Glucan[c] % | Recovery[d] % | Protein[e] % | Starch[f] % |
| Flour-2[b] | 11.50 | Example 1 | 28.6 | 34.6 | 81.7 | 5.2 | 43.2 |
| | | Example 2 | 26.6 | 40.4 | 89.4 | 5.2 | 38.1 |
| | | Example 3 | 25.0 | 39.1 | 82.6 | 4.9 | 37.5 |
| | | Example 4 | 16.4 | 58.9 | 84.0 | 4.9 | 17.6 |
| | | Example 5 | 16.0 | 60.3 | 81.3 | 4.9 | 16.6 |
| | | Example 6 | 20.1 | 51.8 | 86.8 | 4.5 | 27.1 |
| | | Example 7 | 23.3 | 46.0 | 90.1 | 4.8 | 30.4 |
| | | Example 8 | 13.9 | 68.4 | 79.6 | 2.5 | 8.7 |
| | | Example 9 | 22.0 | 47.7 | 88.6 | 4.4 | 29.9 |
| | | Example 10 | 20.0 | 56.1 | 77.8 | 3.6 | 20.9 |
| | | Example 11 | 25.9 | 40.7 | 89.3 | 5.4 | 33.9 |
| OATS | | | | | | | |
| Flour-1 | 3.63 | Example 1 | 12.4 | 24.8 | 79.7 | 22.5 | 25.3 |
| | | Example 2 | 14.4 | 26.4 | 100.0 | 21.5 | 22.2 |
| | | Example 4 | 10.3 | 31.1 | 85.8 | 22.7 | 18.8 |
| | | Example 5 | 10.4 | 30.1 | 83.2 | 24.2 | 22.0 |
| | | Example 10 | 11.7 | 32.9 | 99.0 | 25.2 | 13.7 |
| | | Example 11 | 13.6 | 26.6 | 97.1 | 25.3 | 16.1 |
| Flour-2 | 7.28 | Example 1 | 20.2 | 31.7 | 81.4 | 21.5 | 18.2 |
| | | Example 2 | 19.4 | 31.2 | 78.6 | 20.4 | 16.7 |
| | | Example 3 | 20.2 | 30.6 | 80.7 | 20.9 | 17.8 |
| | | Example 4 | 16.1 | 38.0 | 78.6 | 20.7 | 13.5 |
| | | Example 5 | 13.3 | 41.0 | 74.9 | 19.5 | 14.3 |
| | | Example 6 | 18.1 | 35.4 | 83.7 | 22.0 | 16.9 |
| | | Example 7 | 20.3 | 30.2 | 79.4 | 21.7 | 18.1 |
| | | Example 8 | 12.3 | 42.3 | 67.3 | 19.3 | 12.6 |
| | | Example 9 | 15.2 | 37.0 | 73.1 | 20.4 | 15.2 |
| | | Example 10 | 14.0 | 44.2 | 79.0 | 21.0 | 6.4 |
| | | Example 11 | 19.4 | 31.6 | 80.7 | 23.8 | 12.3 |

[a]Flour produced by pin-milling the pearled grains.
[b]Flour produced by further processing the Flour-1 by additional milling and air-classification.
[c]Determined by the Megazyme procedure Method 995.16 (approved by the American Association of Cereal Chemists) using their analysis kit.
[d]% Recovery = (weight of fiber concentrate × % beta-glucan of fiber concentrate) × 100/(raw-material wt × % beta-glucan of raw material)
[e]Protein % = % N × 6.25; N content was determined by Leco procedure (LECO FP-428 Nitrogen determinator, LECO Corporation, St. Joseph, MI).
[f]Determined by the Megazyme procedure (approved by the American Association of Cereal Chemists, AACC method 32-33) using their analysis kit.

Discussion

The aqueous organic solvent such as ethanol utilized during mixing and enzyme treatment should be used at a concentration to permit solubilization/hydrolysis of the starch and protein but to prevent solubilization of beta-glucans and high molecular weight starch hydrolysis products which may otherwise cause thickening of the slurry. While the preferred concentration of ethanol in water is about 40-60% (v/v), ethanol concentrations of 10-100% can be used depending upon the particular protocol followed. Ethanol concentrations below 30% resulted in gradual thickening of flour-ethanol slurry during mixing (perhaps due to hydration of beta-glucan), which in turn caused technical difficulties during separation including the clogging of a separation screen or filter. Ethanol concentrations above 60% substantially reduced the extent of enzyme hydrolysis of starch and protein and resulted in higher starch concentrations in the fiber/beta-glucan concentrate. Ethanol concentrations above 90% were found to be unsuitable for enzyme hydrolysis. Food grade ethanol is preferred when the product is intended for human consumption.

The flour is mixed with the ethanol until a substantially homogeneous slurry is formed. The time required for mixing depends on the mixing speed and equipment. Sufficient ethanol should be used to provide for easy handling of the slurry. Ratios of flour to ethanol in the range of 1:2-1:10 were found effective. Generally, a greater volume of ethanol is required when the starting material has a smaller particle size. The reaction is preferably carried out at room temperature.

The data indicated that the use of protease enzyme substantially increased the beta-glucan concentration of the fiber/beta-glucan concentrate as compared to the blank. A beta-glucan concentration up to 61% in barley and 41% in oat was reached.

Beta-glucan content of the flour/raw-material influences the beta-glucan content of the fiber residue.

The influence of particle size is highly pronounced Regardless of the beta-glucan content of flour, when 95-97% of the flour is reduced below 250 microns, the beta-glucan concentration of the fiber residue increased to 32-34% (db) in both barley and oat.

The invention claimed is:

1. A method of concentrating beta-glucan (BG) from plant materials comprising the steps of:
   a) mixing and incubating a plant material flour with a solution of ethanol and water wherein the ethanol is at a concentration of 40-90% (v/v) in the water in a single step with any one of or a combination of amylase or protease enzymes to form a flour/ethanol slurry wherein the amylase or protease are active within the ethanol to hydrolyze starch and protein respectively from the plant material flour without beta-glucan being solubilized within the flour/ethanol slurry; and b) separating the flour/ethanol slurry from step a) to form a filtrate portion and a retentate portion;

wherein the retentate portion has a concentrated beta-glucan content and a reduced starch or protein content.

2. A method of concentrating beta glucan (BG) from plant materials comprising the steps of:
   a) mixing and incubating a plant material flour with a solution of ethanol and water wherein the ethanol is at a concentration of 40-90% (v/v) in the water in a single step to form a first flour/ethanol slurry;
   b) separating the first flour/ethanol slurry from step a) to form a filtrate portion and a retentate portion;
   c) mixing and incubating the retentate portion from step b) with a solution of ethanol and water wherein the ethanol is at a concentration of 40-90% (v/v) in the water in a single step in the presence of any one of or a combination of amylase or protease enzymes to form a second flour/ethanol slurry wherein the amylase or protease are active within the ethanol to hydrolyze starch and protein respectively from the plant material flour without beta-glucan being solubilized within the second flour/ethanol slurry; and,
   d) separating the second flour/ethanol slurry from step c) to form a second filtrate portion and a second retentate portion wherein the second retentate portion has a concentrated beta-glucan content and a reduced starch or protein content.

3. A method as in any one of claims 1 or 2 wherein the plant flour is selected from any one or a combination of barley and oats.

4. A method as in claim 1 wherein the ethanol is at a concentration in water of 40-50% (v/v).

5. A method as in any one of claims 1 or 2 wherein incubation is conducted at 15-85° C.

6. A method as in any one of claims 1 or 2 wherein incubation is conducted at room temperature.

7. A method as in any one of claims 1 or 2 wherein the plant material flour in step a) has a particle size distribution wherein >80% of the flour particles are <250 microns.

8. A method as in any one of claims 1 or 2 wherein the plant material flour in step a) has a particle size distribution wherein >85% of the flour particles are <250 microns.

9. A method as in any one of claims 1 or 2 wherein the plant material flour in step a) has a particle size distribution wherein >90% of the flour particles are <250 microns.

10. A method as in any one of claims 1 or 2 wherein the plant material flour in step a) has a particle size distribution wherein >95% of the flour particles are <250 microns.

11. A method as in any one of claims 1 or 2 wherein the flour/ethanol slurry is separated by a screen having a screen mesh size between 40-250 microns.

12. A method as in claim 11 wherein the screen mesh size is between 40-75 microns.

13. A method as in any one of claims 1 or 2 wherein the flour to ethanol ratio is 1:2 to 1:10 (w/v).

14. A method of any one of claims 1 or 2 further comprising subjecting the retentate portion of step b) to at least one subsequent wash with a solution of ethanol and water wherein the ethanol is at a concentration of 40-90% (v/v) in the water and separation to form subsequent filtrate and retentate portions.

15. A method as in claim 14 wherein the subsequent wash includes incubating the mixture with any one of or a combination of amylase or protease enzymes.

16. A method as in any one of claims 1 or 2 wherein the filtrate portion is further evaporated to form a distillate portion containing ethanol and a product solids portion containing starch and ethanol solubles.

17. A method as in claim 1 or 2 wherein the filtrate portion is further evaporated to form a distillate containing ethanol and a product solids portion containing dextrin, protein hydrolysates and ethanol solubles.

18. A method as in claim 2 wherein the second retentate portion from step d) has a BG concentration of greater than 40%.

* * * * *